United States Patent [19]
Yokota et al.

[11] Patent Number: 6,054,609
[45] Date of Patent: Apr. 25, 2000

[54] METHOD OF SEPARATING ISOMERS OF NITROTOLUIC ACID

[75] Inventors: Keiichi Yokota; Ikuo Ito; Seiji Takeuchi, all of Ibaraki, Japan

[73] Assignee: Sumikin Chemical Co., Ltd., Tokyo, Japan

[21] Appl. No.: 09/194,018

[22] PCT Filed: Jan. 26, 1998

[86] PCT No.: PCT/JP98/00277
§ 371 Date: Nov. 19, 1998
§ 102(e) Date: Nov. 19, 1998

[87] PCT Pub. No.: WO98/42654
PCT Pub. Date: Oct. 1, 1998

[30] Foreign Application Priority Data

Mar. 21, 1997 [JP] Japan ................................ 9-068676

[51] Int. Cl.⁷ ........................ C07C 205/06; C07C 205/57
[52] U.S. Cl. ............................................................ 562/434
[58] Field of Search ............................................. 562/434

[56] References Cited

U.S. PATENT DOCUMENTS 3,857,881  12/1974  Saiki et al. ............................... 260/525

FOREIGN PATENT DOCUMENTS 50-7592  3/1975  Japan .

OTHER PUBLICATIONS

Peltier, CA 52:9016 f, No month provided 1958.

*Primary Examiner*—Rosalynd Keys
*Attorney, Agent, or Firm*—Wenderoth, Lind & Ponack, L.L.P.

[57] ABSTRACT

A method of separating 3-nitro-o-toluic acid and 5-nitro-o-toluic acid from a mixture of said isomers, comprising producing salts by adding an aromatic organic base, for example, aniline or pyridine, to the said mixture, separating said salts into solids and a mother liquor, by taking advantage of the difference in solubilities between the said salts to water or a mixed solvent consisting of water and a water-soluble organic compound, for example, methanol, and, further, recovering 3-nitro-o-toluic acid from the mother liquor and 5-nitro-o-toluic acid from the solids.

4 Claims, No Drawings

METHOD OF SEPARATING ISOMERS OF NITROTOLUIC ACID

BACKGROUND OF THE INVENTION

1. Field of the Invention

The present invention relates to a method of separating isomers of nitrotoluic acid. More particularly, the present invention relates to a method of separating 3-nitro-o-toluic acid and 5-nitro-o-toluic acid into two individual components at high yields by producing salts by way of adding an aromatic organic base to a mixture of 3-nitro-o-toluic acid and 5-nitro-o-toluic acid and efficiently recovering both 3-nitro-o-toluic acid and 5-nitro-o-toluic acid by taking advantage of the difference between said salts in their solubility to water or a mixture of water and a water-soluble organic compound.

2. Descriptions of the Related Art

3-Nitro-o-toluic acid and 5-nitro-o-toluic acid are highly important compounds as raw materials for pharmaceuticals, agrochemicals, dyestuff, etc.

There has been known the process of nitrating o-toluic acid for manufacturing 3-nitro-o-toluic acid and 5-nitro-o-toluic acid. In such a nitration process, the reaction gives, as its product, a mixture of 3-nitro-o-toluic acid and 5-nitro-o-toluic acid, which need to be separated from each other.

3-Nitro-o-toluic acid and 5-nitro-o-toluic acid both have high melting points and high boiling points, hence it is rendered quite difficult to separate them by distillation or the like. As a method of separating the isomers from each other, a troublesome method like the fractional recrystallization method which is described in Japanese Patent Publication No. 1975-7592 is necessitated. Even if the recrystallization method is employed, it is still difficult to accomplish the separation in a single step.

Besides, it is possible to change the production ratio between 3-nitro-o-toluic acid and 5-nitro-o-toluic acid by altering conditions of the nitration reaction. For instance, when severe reaction conditions are selected, the ratio of the amount of 5-nitro-o-toluic acid produced to the amount of 3-nitro-o-toluic acid produced is improved, and by recrystallizing the nitration product thus obtained, there can be obtained 5-nitro-o-toluic acid having a high purity. In the case where mild reaction conditions are selected, however, the amount of 3-nitro-o-toluic acid produced never exceeds the amount of 5-nitro-o-toluic acid produced, and hence it is impossible to produce 3-nitro-o-toluic acid at a high yield.

Another generally conceivable method of producing 3-nitro-o-toluic acid and 5-nitro-o-toluic acid is the separation by adjusting the pH in the precipitation process using an acid. It is, however, impossible to produce both 3-nitro-o-toluic acid and 5-nitro-o-toluic acid in satisfactory yields and qualities.

For instance, even though it is possible to produce 5-nitro-o-toluic acid at a high yield by the precipitation process (which is performed by, after dissolving a metallic salt of nitrotoluic acid into a solution, adjusting the pH value of the solution by adding an acid), 3-nitro-o-toluic acid cannot be produced at a high yield by recovering crystals from the mother liquor from which 5-nitro-o-toluic acid has been already separated since 5-nitro-o-toluic acid is deposited in the first place.

The inventors of the present application, after having studied methods of overcoming the aforementioned difficulties and separating from a mixture of 3-nitro-o-toluic acid and 5-nitro-o-toluic acid both of these isomers easily at high yields, discovered that the salts produced from the isomers by adding an aromatic organic base to nitro-o-toluic acid exhibit their inherent solubilities to water or a mixed solvent consisting of water and a water-soluble organic compound. The inventors observed that the solubilities of 3-nitro-o-toluic acid and 5-nitro-o-toluic acid differed from each other to a great extent, and discovered that both 3-nitro-o-toluic acid and 5-nitro-o-toluic acid can be recovered at high yields easily and efficiently by separating such a solution into solids and a liquid. The inventors have thus completed the present invention.

SUMMARY OF THE INVENTION

The present invention relates to a method of separating isomers of nitrotoluic acid which comprises adding an aromatic organic base to a mixture of 3-nitro-o-toluic acid and 5-nitro-o-toluic acid to produce salts thereof in the presence of water or a mixed solvent consisting of water and a water-soluble organic compound, separating the resulting mixture into solids and a mother liquor, and recovering 3-nitro-o-toluic acid from the mother liquor and 5-nitro-o-toluic acid from the solids respectively.

DESCRIPTION OF THE PREFERRED EMBODIMENTS

According to the present invention, the advantageous way of obtaining the mixture of 3-nitro-o-toluic acid and 5-nitro-o-toluic acid, which constitutes the object of the isomer separating treatment, is the nitration reaction using o-toluic acid as the reactant. Nonetheless, the practicable process is not limited thereto.

There can be cited as examples of the nitrating agent concentrated nitric acid, fuming nitric acid, mixed acid, and the like. Either nitrating agent is used by 0.5 to 5 times in mol as against the raw material.

As the reaction solvent, sulfuric acid may be utilized as the solvent in the case of a mixed acid, and any organic solvent may be utilized so far as it does not hinder a stable progress of the reaction. Some examples of such organic solvents are acetic acid, methylene chloride and chloroform. The minimum required quantity of a solvent is no less than what will be sufficient to agitate the mixture of nitration reaction. Generally, it is 1 to 20 times as much as the raw material by weight.

The reaction is controlled by either dropping a mixed acid or nitric acid as the nitrating agent onto the raw material charged into the reaction vessel or adding o-toluic acid as the raw material into the reaction vessel charged with a nitrating agent. The reaction temperature may be controlled within the range of 0° C. to 100° C. and the duration of dropping or adding may be determined to be at a level suitable for the cooling capacity, usually between 0.5 to 24 hrs. Although the reaction may be terminated immediately after the end of the dropping or adding step, the reaction may be terminated preferably after having continued the agitation for 0.5 to 5 hrs.

According to the present invention, the nitration reaction product which becomes the raw material for the isomers separating step is, after the nitration reaction is ended, separated by a conventional method, such as the centrifugal separation, the filtration under reduced pressure, and the pressure filtration, and the wet cake thereby obtained is processed as it is or in the dried form or, in some cases, after being washed with water.

According to the present invention, salts are caused to be formed in the presence of water or a mixed solvent consisting of water and a water-soluble organic compound (hereinafter may be referred to simply as "a mixed solvent") by adding an aromatic organic base to the mixture of nitrotoluic acids thus obtained, and 3-nitro-o-toluic acid and 5-nitro-o-toluic acid are separated from each other by taking advantage of the different solubilities of the salts thereby produced to water or the mixed solvent. Hence, it is advantageous to add the aromatic organic base in the presence of water or the mixed solvent used for the separating step, although the solvent may be added after the aromatic organic base has been added.

Although there is no limitation to the kind of aromatic organic base used for production of salts so long as it is capable of producing salts with nitrotoluic acid, there can be cited as examples of the aromatic organic bases which can be used for the said purpose anilines such as aniline, alkyl aniline, and N-alkyl aniline, pyridines such as pyridine and alkylpyridine, and quinolines such as quinoline, isoquinoline and quinaldine. Out of the said aromatic organic bases, preferable ones are monocyclic aromatic organic bases, i.e., anilines and pyridines, and particularly preferable ones are aniline and pyridine.

The amount of an aromatic organic base to be used is preferably 0.9 to 5 times in mol as against the total acid in the nitration reactant which becomes the raw material for the isomers separating treatment. If the aromatic organic base is used in an excessive quantity, economics is impaired, and if it is, by contrast, used in too low a quantity, the salt production does not take place to a sufficient extent and the separation is carried out only insufficiently with the result that the qualities of 3-nitro-o-toluic acid and 5-nitro-o-toluic acid are deteriorated.

The treatment temperature is determined in accordance with the treating conditions, since the amounts of salts produced from the reaction between nitrotoluic acid and the aromatic organic base vary with the amount of the solvent and the mixing ratio between water and a water-soluble organic compound. The treatment is carried out usually at a temperature not higher than 50° C. If the temperature is too high, production of salts does not take place between nitrotoluic acid and the aromatic organic base, and the separation of 3-nitro-o-toluic acid and 5-nitro-o-toluic acid from each other cannot be carried out to a sufficient extent, with the result that the qualities of both 3-nitro-o-toluic acid and 5-nitro-o-toluic acid are deteriorated.

The treatment may be carried out by continuing the agitation for 0.5 to 24 hrs. after an aromatic organic base is added.

The said treatment may be performed after neutralizing residual sulfuric acid and nitric acid in the nitration reactant with such chemicals as sodium hydroxide, potassium hydroxide and ammonia.

The solvent utilized in the isomers separating step is water or a mixture of water and a water-soluble organic compound. Although the separation of isomers of nitrotoluic acid can be accomplished by using either one of the said solvents, the solubilities of salts produced by the reaction between nitrotoluic acid and an aromatic organic base are higher in the case of the mixed solvent, and, therefore, the mixed solvent is preferably used in cases where it is desirable to minimize a quantity of the solvent and increase the volume efficiency.

There is not imposed any limitation on the kind of the water-soluble organic compound which is utilized in the form of a mixture with water so far as it is water-soluble. Some examples of suitable water-soluble organic compounds are methanol, ethanol, isopropanol, acetone, tetrahydrofuran and dioxan.

The mixing ratio between water and the water-soluble organic compound is determined in accordance with the adopted treating conditions, since the amounts of salts produced by the reaction between nitrotoluic acid and an aromatic organic salt vary with the temperature and the quantity of the solvent. Usually, the water-soluble organic compound is used by the ratio of 0 to 50 times by weight to water. Although the volume efficiency is improved in case an excessive amount of a water-soluble organic compound is used, the use of an excessive water-soluble organic compound is not desirable, since it results in a decline in the operability and deterioration of the quality of 3-nitro-o-toluic acid to be produced from the mother liquor.

While the amount of the solvent is determined in accordance with the treating conditions, since the amount dissolved into the solvent of the salts produced by the reaction between nitrotoluic acid and an aromatic organic base vary with the mixing ratio between water and the water-soluble organic compound, the water-soluble organic compound is used usually at the ratio of 1 to 30 times by weight to the nitration reaction product, which becomes the raw material for the isomers separating step. If the amount of the solvent is excessive, it is not economical due to the decline of the volume efficiency, and, worse still, in some cases, elution of 5-nitro-o-toluic acid into the mother liquor increases to an extent that the quality of 3-nitro-o-toluic acid is deteriorated. On the contrary, if the amount of the solvent is too little, the operability declines and the residual 3-nitro-o-toluic acid content of the solids deteriorates the quality of 5-nitro-o-toluic acid, which is by no means desirable.

Because the salts produced in the presence of water or a mixed solvent are in the slurry form, such a slurry is subjected to a conventional separating method, for example, the centrifugal separation, the filtration under reduced pressure, the pressure filtration, and decantation, for separating solids from the mother liquor.

The solids and the mother liquor thereby separated can be both used as the raw materials, without being subjected to a further process so far as it does not end up with any objectionable result.

In the process of recovering 3-nitro-o-toluic acid and 5-nitro-o-toluic acid, crystals are caused to separate from the mother liquor or the solids dispersed in water by adding sulfuric acid, hydrochloric acid or another acid to each of them. By way of recovering thus obtained crystals by a conventional means, for example, the centrifugal separation, the filtration under reduced pressure, the pressure filtration or decantation, 3-nitro-o-toluic acid is obtained from the mother liquor and 5-nitro-o-toluic acid from the solids, respectively.

In the case where 3-nitro-o-toluic acid and 5-nitro-o-toluic acid having higher purities are wanted, the obtained crystals may be readily purified by a recrystallization process and the like.

The present invention is more specifically explained in reference to the following examples. The analysis for the purity of nitrotoluic acid was carried out by first methylesterifying nitrotoluic acid with diazo methane and referring the obtained specimen to gas chromatography using an internal standard (the internal standard: naphthalene). The symbol "%" cited in each Example denotes "% by weight" unless otherwise indicated.

MANUFACTURING EXAMPLE 1

68 g. of o-toluic acid and 176.5 g. of 98%-concentration sulfuric acid were introduced into a flask having an internal capacity of 500 ml, which was provided with a stirrer, a thermometer and a reflux condenser. While the internal temperature of the flask was maintained at 50° C., 62 g. of 61%-concentration nitric acid was dropped into the flask over a period of 2.3 hrs. After the dropping was completed, the content of the flask was agitated for 2 hrs. at 50° C.

Upon completion of the reaction, the flask was cooled and the reaction product was added to 250 g. of water. Then, by filtering out the crystals, 155.6 g. of a nitration reaction product was obtained in the form of wet cake. Part of this nitration reaction product was dried and analyzed by gas chromatography for its components. The analytical results indicated that the concentrations of o-toluic acid, 3-nitro-o-toluic acid, and 5-nitro-o-toluic acid in the wet cake were 2.4%, 23.3% and 27.6% respectively. The ratio of the amount of 3-nitro-o-toluic acid obtained to the amount of 5-nitro-o-toluic acid obtained was 5 to 6.

EXAMPLE 1

64 g. of water was added to 8.01 g. of the wet cake obtained in Manufacturing Example 1. After 3.77 g. of aniline was added to the slurry, the mixture was agitated for 1 hr. at room temperature. Then, the mixture was filtered to be separated into a mother liquor and solids. The pH of the mother liquor was adjusted to 1 with sulfuric acid and the crystals thereby deposited were filtered out and dried into 2.11 g. of cake. The obtained cake was analyzed by gas chromatography for its components. The analysis turned out to be 6.0% of o-toluic acid, 78.6% of 3-nitro-o-toluic acid, and 9.5% of 5-nitro-o-toluic acid. The ratio of the amount of 3-nitro-o-toluic acid obtained to the amount of 5-nitro-o-toluic acid obtained was 8 to 1. The recovery yield of 3-nitro-o-toluic acid was 88.9 mol %.

To the solids, on the other hand, 20 g. of water was added and by adjusting the pH of the slurry with sulfuric acid, crystals were caused to deposit. Then, by filtering out and drying the deposited crystals, 2.04 g. of cake were obtained. The obtained cake was analyzed by gas chromatography for its components. The analysis turned out to be 0.7% of o-toluic acid, 6.5% of 3-nitro-o-toluic acid, and 91.1% of 5-nitro-o-toluic acid. The ratio of the amount of 3-nitro-o-toluic acid obtained to the amount of 5-nitro-o-toluic acid obtained was 1 to 13. The recovery ratio of 5-nitro-o-toluic acid was 84.2 mol %. The test results are shown in Table 1.

EXAMPLE 2

Except that pyridine was used as an aromatic organic base in place of aniline and 16 g. of water and 3.83 g. of pyridine were added to 8.05 g. of wet cake, salts were caused to be produced in the same manner as in Example 1. By following the same procedure as in Example 1 thenceforth, 2.13 g. of cake was obtained from the mother liquor and 2.08 g. of cake from the solids.

The analysis of the cake obtained from the mother liquor were 5.6% of o-toluic acid, 80.8% of 3-nitro-o-toluic acid, and 11.5% cf 5-nitro-o-toluic acid. The ratio of the amount of 3-nitro-o-toluic acid obtained to the amount of 5-nitro-o-toluic acid obtained was 7 to 1. The recovery ratio of 3-nitro-o-toluic acid was 91.8 mol %.

On the other hand, the analysis of the cake from the solids by gas chromatography turned out to be 0.7% of o-toluic acid, 5.1% of 3-nitro-o-toluic acid, and 93.2% of 5-nitro-o-toluic acid. The ratio of the amount of 3-nitro-o-toluic acid obtained to the amount of 5-nitro-o-toluic acid obtained was 1 to 18. The recovery ratio of 5-nitro-o-toluic acid was 87.4 mol %. The test results are shown in Table 1.

MANUFACTURING EXAMPLE 2

272 g. of o-toluic acid, 196 g. of 98%-concentration sulfuric acid, and 1000 ml of methylene chloride were introduced into a flask having an internal capacity of 2 liters which was provided with a stirrer, a thermometer and a reflux condenser. While the internal temperature of the flask was maintained at 40° C., 154 g. of 98%-concentration nitric acid was dropped into the flask over a period of 1.3 hrs. After the dropping was completed, the content of the flask was agitated for 1 hr. at 40° C.

Upon completion of the reaction, the reactant liquid was concentrated by evaporating methylene chloride. After adding 1000 g. of water to the obtained liquid, crystals were filtered out and dried into 390 g. of a nitration reaction product.

The analysis of the said nitration reaction product were 0.5% of o-toluic acid, 36.2% of 3-nitro-o-toluic acid, and 54.1% of 5-nitro-o-toluic acid. The ratio of the amount of 3-nitro-o-toluic acid obtained to the amount of 5-nitro-o-toluic acid obtained was 2 to 3.

EXAMPLE 3

After adding 20 g. of water, 10 g. of methanol, and, then, 7.03 g. of aniline to 10 g. of the nitration reaction product obtained in Manufacturing Example 2, and the mixture was agitated for 1 hr. at 20° C. Then, the mixture was filtered to be separated into a mother liquor and solids. The pH of the mother liquor was adjusted to 1.4 with sulfuric acid and the crystals thereby deposited were filtered out and dried into 4.60 g. of cake. The obtained cake was analyzed by gas chromatography for its components. The analysis turned out to be 0.8% of o-toluic acid, 74.7% of 3-nitro-o-toluic acid, and 8.9% of 5-nitro-o-toluic acid. The ratio of the amount of 3-nitro-o-toluic acid obtained to the amount of 5-nitro-o-toluic acid obtained was 8 to 1. The recovery yield of 3-nitro-o-toluic acid was 95.1 mol %.

On the other hand, by adding 40 g. of water to the solids and adjusting the pH of the slurry to 1.3, and, then, filtering out and drying the deposited solids, 4.79 g. of cake was obtained. The obtained cake was analyzed by gas chromatography for its components. The analytical result indicated that the concentrations of 3-nitro-o-toluic acid, and 5-nitro-o-toluic acid in the cake were 2.0% and 94.5%. The ratio of 3-nitro-o-toluic acid to 5-nitro-o-toluic acid was 1 to 47. The recovery yield of 5-nitro-o-toluic acid was 83.7 mol %. The test results are shown in Table 2.

EXAMPLES 4, 5, AND 6

Except that the quantities of water, methanol and aniline and the temperature were altered to those which are shown in Table 2, the isomers were separated according to the same procedure as in Example 3. The test results are shown in Table 2.

MANUFACTURING EXAMPLE 3

13.6 g. of o-toluic acid and 35.3 g. of 98%-concentration sulfuric acid were introduced into a flask having an internal capacity of 100 ml, which was provided with a stirrer, a thermometer and a reflux condenser. While the internal temperature of the flask was maintained at 90 to 100° C., 15.5 g. of 61%-concentration nitric acid was dropped into the flask over a period of 2 hrs. After the dropping was completed, the content of the flask was agitated for 2 hr. at 100° C.

Upon completion of the reaction, the reactant liquid was cooled. After adding 100 g. of water to the obtained liquid, crystals were filtered out and dried into 17.6 g. of a nitration reaction product. The obtained nitration reaction product was analyzed by gas chromatography for its components. The analysis of the nitration reaction product thereby obtained were 0.6% of o-toluic acid, 22.7% of 3-nitro-o-toluic acid, and 46.6% of 5-nitro-o-toluic acid. The ratio of the amount of 3-nitro-o-toluic acid obtained to the amount of 5-nitro-o-toluic acid obtained was 1 to 2.

COMPARATIVE EXAMPLE 1

6 g. of ethanol was added to 2.97 g. of the nitration reaction product obtained in Manufacturing Example 3, which was then melted by heating. And the crystals deposited after the liquid had been cooled to 0° C. were filtered out and dried into 0.54 g. of cake.

The obtained cake was analyzed by gas chromatography for its components. The analytical result indicated that the concentrations of o-toluic acid, 3-nitro-o-toluic acid, and 5-nitro-o-toluic acid in the cake were 0.2%, 2.2% and 97.2%, respectively. The ratio of the amount of 3-nitro-o-toluic acid obtained to the amount of 5-nitro-o-toluic acid obtained was 1 to 44. The recovery ratio of 5-nitro-o-toluic acid was 37.9 mol %. Although 5-nitro-o-toluic acid was obtained via the recrystallization step at such a high purity by means of carrying out the nitration reaction under severe conditions like 90 to 100° C., the recovery ratio was quite low and the process failed to produce 3-nitro-o-toluic acid at a high purity.

COMPARATIVE EXAMPLE 2

40 g. of water was added to 8.04 g. of the wet cake obtained in Manufacturing Example 1, and the prepared slurry was agitated for 1 hr. at room temperature with the pH adjusted to 11 with 48% sodium hydroxide. Thereupon, crystals were caused to deposit by adjusting the pH of the slurry to 4.5 by adding 10% sulfuric acid, and the crystals thereby deposited were then filtered out and dried into 1.65 g. of cake. The obtained cake was analyzed by gas chromatography for its components. The analytical result indicated that the concentrations of o-toluic acid, 3-nitro-o-toluic acid, and 5-nitro-o-toluic acid in the cake were 3.9%, 1.1%, and 91.2%, respectively. The ratio of the amount of 3-nitro-o-toluic acid obtained to the amount of 5-nitro-o-toluic acid obtained was 1 to 83. The recovery ratio of 5-nitro-o-toluic acid was 67.8 mol %.

To the filtrate, on the other hand, sulfuric acid was added to adjust the pH to 1.9, and there were deposited crystals. The crystals thereby deposited were filtered out and dried into 2.59 g. of cake. The obtained cake was analyzed by gas chromatography for its components. The analytical result indicated that the concentrations of o-toluic acid, 3-nitro-o-toluic acid, and 5-nitro-o-toluic acid in the cake were 5.3%, 68.6% and 22.6%, respectively. The ratio of the amount of 3-nitro-o-toluic acid obtained to the amount of 5-nitro-o-toluic acid obtained was 3 to 1. The test results are shown in Table 1 in comparison with the test results of Examples 1 and 2.

Although 5-nitro-o-toluic acid was obtained at a high yield from the crystals which had been separated in the first place, 3-nitro-o-toluic acid could not be recovered at a high yield from the filtrate from which 5-nitro-o-toluic acid had been separated.

COMPARATIVE EXAMPLE 3

10 g. of methanol was added to 10 g. of the nitration reaction product in the cake form (2.5% of o-toluic acid, 24.6% of 3-nitro-o-toluic acid and 31.2% of 5-nitro-o-toluic acid) which had been obtained according to the same procedure as in Manufacturing Example 1. After melting the nitration reaction product by heating, the solution was cooled to room temperature to deposit crystals, which were then filtered out and dried into 4.04 g. of cake. The analytical result indicated that the concentrations of o-toluic acid, 3-nitro-o-toluic acid, and 5-nitro-o-toluic acid in the cake were 1.0%, 43.7% and 59.1%, respectively. The ratio of the amount of 3-nitro-o-toluic acid obtained to the amount of 5-nitro-o-toluic acid obtained was 5 to 7. The test results are shown in Table 3.

COMPARATIVE EXAMPLES 4, 5, AND 6

Except that the kinds and quantities of solvent, utilized for recrystallization were altered to those which are shown in Table 3, the isomers were separated according to the same procedure as in Comparative Example 3. The test results are shown in Table 3. The method of recrystallizing utilizing solvents failed to materially improve the ratios of the isomers produced in spite of such attempts made with varied solvents.

Separation of 3-nitro-o-toluic acid and 5-nitro-o-toluic acid from the mixture thereof used to be accompanied by difficulties and could not be accomplished by recrystallization or adjustment of the pH value in the precipitation process using an acid. According to the present invention, both of the said isomers can be separated at high yields and high recovery ratios by means of causing salts to be produced by adding an aromatic organic base to the mixture of those isomers and taking advantage of the difference in the solubilities of the salts thereby produced to water or the mixture of water and a water-soluble organic compound. Hence, the method disclosed in the present invention is an excellent method to recover 3-nitro-o-toluic acid and 5-nitro-o-toluic acid which are both useful raw materials for pharmaceuticals, agrochemicals and dyestuff.

TABLE 1

LEGEND: "o-TA" stands for o-toluic acid.
"3-N-o-TA" stands for 3-nitro-o-toluic acid.
"5-N-o-TA" stands for 5-nitro-o-toluic acid.

|  |  | Example 1 | Example 2 | Comparative Example 2 |
|---|---|---|---|---|
| Treating Conditions | Nitration reaction product (g) | 8.01 | 8.05 | 8.04 |
|  | Water (g) | 64 | 16 | 40 |
|  | Base Aniline (g) | 3.77 | — | — |
|  | Pyridine (g) | — | 3.83 | — |

TABLE 1-continued

LEGEND: "o-TA" stands for o-toluic acid.
"3-N-o-TA" stands for 3-nitro-o-toluic acid.
"5-N-o-TA" stands for 5-nitro-o-toluic acid.

|  |  |  | Example 1 | Example 2 | Comparative Example 2 |
|---|---|---|---|---|---|
|  |  | Sodium hydroxide | — | — | * |
|  |  | Temperature (° C.) | Room temp. | Room temp. | Room temp. |
| Results of Separation | From Mother liquor | Recovered cake (g) | 2.11 | 2.13 | 2.59 |
|  |  | Conc. o-TA | 6.0 | 5.6 | 5.3 |
|  |  | % 3-N-o-TA | 78.6 | 80.8 | 68.6 |
|  |  | 5-N-o-TA | 9.5 | 11.5 | 22.6 |
|  |  | 3-N-o-TA to 5-N-o-TA ratio | 8:1 | 7:1 | 3:1 |
|  |  | 3-N-o-TA recovery ratio (mol %) | 88.9 | 91.8 | 95.2 |
|  | From Solids | Recovered cake (g) | 2.04 | 2.08 | 1.65 |
|  |  | Conc. o-TA | 0.7 | 0.7 | 3.9 |
|  |  | % 3-N-o-TA | 6.5 | 5.1 | 1.1 |
|  |  | 5-N-o-TA | 91.1 | 93.2 | 91.2 |
|  |  | 3-N-o-TA to 5-N-o-TA ratio | 1:13 | 1:18 | 1:83 |
|  |  | 5-N-o-TA recovery yield (mol %) | 84.2 | 87.4 | 67.8 |

*After NaOH was added to the extent that the pH became 11, the pH value was adjusted to 4.5 with sulfuric acid.

TABLE 2

|  |  |  | Example 3 | Example 4 | Example 5 | Example 6 |
|---|---|---|---|---|---|---|
| Treating conditions | Nitration reaction product (g) |  | 10 | 10 | 10 | 10 |
|  | Solvents | Water (g) | 20 | 20 | 20 | 25 |
|  |  | Methanol (g) | 10 | 10 | 10 | 5 |
|  | Aniline (g) |  | 7.03 | 6.08 | 8.09 | 7.06 |
|  | Temperature (° C.) |  | 20 | 20 | 20 | 30 |
| Results of Separation | From Mother liquor | Recovered cake (g) | 4.60 | 3.92 | 5.50 | 3.82 |
|  |  | Conc. o-TA | 0.8 | 0.9 | 0.6 | 0.8 |
|  |  | % 3-N-o-TA | 74.7 | 83.1 | 62.3 | 82.4 |
|  |  | 5-N-o-TA | 8.9 | 7.8 | 8.0 | 11.0 |
|  |  | 3-N-o-TA to 5-N-o-TA ratio | 8:1 | 11:1 | 8:1 | 7:1 |
|  |  | 3-N-o-TA recovery ratio (mol %) | 95.1 | 90.2 | 94.7 | 87.1 |
|  | From Solids | Recovered cake (g) | 4.79 | 4.81 | 4.76 | 5.16 |
|  |  | Conc. o-TA | trace | trace | trace | trace |
|  |  | % 3-N-o-TA | 2.0 | 2.8 | 2.5 | 6.9 |
|  |  | 5-N-o-TA | 94.5 | 96.5 | 96.6 | 91.8 |
|  |  | 3-N-o-TA to 5-N-o-TA ratio | 1:47 | 1:34 | 1:39 | 1:13 |
|  |  | 5-N-o-TA recovery yield (mol %) | 83.7 | 85.8 | 85.0 | 87.6 |

TABLE 3

|  |  |  | Comparat. Example 3 | Comparat. Example 4 | Comparat. Example 5 | Comparat. Example 6 |
|---|---|---|---|---|---|---|
| Treating conditions | Wet cake (g) |  | 10 | 10 | 10 | 10 |
|  | Solvents | Kind | Methanol | Ethyl acetate | Isopropyl ether | Acetic acid |
|  |  | Amount added (g) | 10 | 10 | 30 | 20 |
| Results of Separation | Recovered cake (g) |  | 4.04 | 1.21 | 2.66 | 3.90 |
|  | Conc. % | o-TA | 1.0 | 0.8 | 0.9 | 1.4 |
|  |  | 3-N-o-TA | 43.7 | 37.0 | 42.7 | 42.1 |
|  |  | 5-N-o-TA | 59.1 | 62.1 | 56.1 | 56.1 |
| 3-N-o-TA to 5-N-o-TA ratio |  |  | 5:7 | 4:7 | 5:6 | 5:6 |

What is claimed is:

1. A method of separating isomers of nitrotoluic acid which comprises (1) adding an aromatic organic base to a mixture of 3-nitro-o-toluic acid and 5-nitro-o-toluic acid to produce salts thereof in the presence of water or a mixed solvent consisting of water and a water-soluble organic compound, (2) separating the resulting mixture into solids and a mother liquor, and (3) recovering 3-nitro-o-toluic acid from the mother liquor and 5-nitro-o-toluic acid from the solids respectively.

2. The method of separating isomers of nitrotoluic acid according to claim 1, wherein the aromatic organic base is aniline or pyridine.

3. The method of separating isomers of nitrotoluic acid according to claim 1, wherein the water-soluble organic compound is methanol.

4. The method of separating isomers of nitrotoluic acid according to claim 2, wherein the water-soluble organic compound is methanol.

* * * * *